United States Patent [19]
Voorberg et al.

[11] Patent Number: 6,083,905
[45] Date of Patent: Jul. 4, 2000

[54] METHOD AND MEANS FOR DETECTING AND TREATING DISORDERS IN THE BLOOD COAGULATION CASCADE

[75] Inventors: Johannes Jacobus Voorberg, Assendelft; Jan Aart van Mourik, Badhoevedorp; Koenraad Mertens, Leiden, all of Netherlands

[73] Assignee: Stichting Sanquin Bloedvoorziening, Amsterdam, Netherlands

[21] Appl. No.: 08/722,240

[22] PCT Filed: Apr. 21, 1995

[86] PCT No.: PCT/NL95/00149

§ 371 Date: Jan. 22, 1997

§ 102(e) Date: Jan. 22, 1997

[87] PCT Pub. No.: WO95/29259

PCT Pub. Date: Nov. 2, 1995

[30] Foreign Application Priority Data

Apr. 22, 1997 [EP] European Pat. Off. ............... 94201116

[51] Int. Cl.7 ............................ A01N 37/18; A61K 35/14
[52] U.S. Cl. .................................. 514/2; 514/21; 514/802; 514/822; 530/381
[58] Field of Search ................................ 530/381; 514/2, 514/21

[56] References Cited

FOREIGN PATENT DOCUMENTS

WO 87/07144  12/1987  WIPO .

OTHER PUBLICATIONS

Dahlback, Haemostasis 24 (2): 193–151 (abstract), 1994.
Bertina et al., Nature 369:64–67, May 5, 1994.
Zoller et al., The Lancet 343:15361538.
B. Dahlback et al., "Inherited resistance to activated protein C is corrected by anticoagulant cofactor activity found to be a property of facor V", Proceedings of the National Academy of Science of USA, vol. 91, Feb. 1994, pp. 1396–1400.

P.J. Fay et al., "Activated Protein C–catalyed Inactivation of Human Factor VIII and Factor VIII", *Journal of Biological Chemistry*, vol. 266, No. 30, Oct. 1991, pp. 20139–20145.

M. Kalafatis et al., "Role of the Membrane in the Inactivation of Factor Va by Activated Protein C*", *Journal of Biological Chemistry*, vol. 268, No. 36, Dec. 25, 1993, pp. 27246–27257.

B. Dahlback et al., "Familial thrombophilia due to a previously unrecognized mechanism characterized by poor anticoagulant response to activated Protein C: Prediction of a cofactor to activated protein C", Proceedings of the National Academy of Science of USA, vol. 90, Feb. 1993, pp. 1004–1008.

J. Voorberg et al., "Association of idiopathic venous thromboembolism with single point–mutation at Arg$^{506}$ of factor V" *The Lancet*, vol. 343, Jun. 18, 1994, pp. 1535–1536.

*Primary Examiner*—Stephanie W. Zitomer
*Attorney, Agent, or Firm*—Hoffmann & Baron, LLP

[57] ABSTRACT

This invention relates to the diagnosis of congenital defects in the anticoagulant protein C system. Methods that are disclosed are based on the detection of mutations at the cleavage sites of coagulation factors that are under control of activated protein C (APC). Diagnostic tests include analysis of the APC-cleavage sites of factor V and factor VIII, by using specific primers to amplify selectively from RNA, cDNA derived from RNA or chromosomal DNA, parts of factor V and factor VIII that contain cleavage sites for APC. Methods that monitor the presence of mutations at the cleavage sites for APC and their utility in the diagnosis of thrombo-embolic disease are disclosed. The invention further discloses methods for correcting the defects detected according to the invention, as well as novel therapeutic agents which can be used in the treatment of bleeding disorders, which agents are based on the "defective" Factor V and Factor VIII proteins leading to the thrombotic disorders described hereinabove.

13 Claims, 7 Drawing Sheets

SEQUENCE LISTING (1) GENERAL INFORMATION:

(iii) NUMBER OF SEQUENCES: 34

(2) INFORMATION FOR SEQ ID NO: 1:

(i) SEQUENCE CHARACTERISTICS:
      (A) LENGTH: 24 base pairs
      (B) TYPE: nucleic acid
      (C) STRANDEDNESS: unknown
      (D) TOPOLOGY: unknown (ii) MOLECULE TYPE: DNA (genomic)

(iii) HYPOTHETICAL: NO (xi) SEQUENCE DESCRIPTION: SEQ ID NO: 1:

TGTAAGAGCA GATCCCTGGA CTCG                                              24

(2) INFORMATION FOR SEQ ID NO: 2:

(i) SEQUENCE CHARACTERISTICS:
            (A) LENGTH: 22 base pairs
            (B) TYPE: nucleic acid
            (C) STRANDEDNESS: unknown
            (D) TOPOLOGY: unknown (ii) MOLECULE TYPE: DNA (genomic)

(iii) HYPOTHETICAL: NO (xi) SEQUENCE DESCRIPTION: SEQ ID NO: 2:

CATCACGTTT CACCTCATCA GG                                                22

(2) INFORMATION FOR SEQ ID NO: 3:

(i) SEQUENCE CHARACTERISTICS:
            (A) LENGTH: 21 base pairs
            (B) TYPE: nucleic acid
            (C) STRANDEDNESS: unknown
            (D) TOPOLOGY: unknown (ii) MOLECULE TYPE: DNA (genomic)

(iii) HYPOTHETICAL: NO (xi) SEQUENCE DESCRIPTION: SEQ ID NO: 3:

ATCAGAGCAG TTCAACCAGG G                                                 21

(2) INFORMATION FOR SEQ ID NO: 4:

(i) SEQUENCE CHARACTERISTICS:
            (A) LENGTH: 18 base pairs
            (B) TYPE: nucleic acid
            (C) STRANDEDNESS: unknown
            (D) TOPOLOGY: unknown (ii) MOLECULE TYPE: DNA (genomic)

(iii) HYPOTHETICAL: NO (xi) SEQUENCE DESCRIPTION: SEQ ID NO: 4:

CTGGTAAAAG ACTTGAAT                                                     18

(2) INFORMATION FOR SEQ ID NO: 5:

(i) SEQUENCE CHARACTERISTICS:
            (A) LENGTH: 21 base pairs
            (B) TYPE: nucleic acid
            (C) STRANDEDNESS: unknown
            (D) TOPOLOGY: unknown (ii) MOLECULE TYPE: DNA (genomic)

(iii) HYPOTHETICAL: NO (xi) SEQUENCE DESCRIPTION: SEQ ID NO: 5:

CTGGTTTCCA TTTTGATCTA C                                                 21

(2) INFORMATION FOR SEQ ID NO: 6:

(i) SEQUENCE CHARACTERISTICS:
            (A) LENGTH: 21 base pairs
            (B) TYPE: nucleic acid (C) STRANDEDNESS: unknown
            (D) TOPOLOGY: unknown (ii) MOLECULE TYPE: DNA (genomic)

(iii) HYPOTHETICAL: NO (xi) SEQUENCE DESCRIPTION: SEQ ID NO: 6:

GTAGATCAAA ATGGAAACCA G                                                       21

(2) INFORMATION FOR SEQ ID NO: 7:

(i) SEQUENCE CHARACTERISTICS:
            (A) LENGTH: 18 base pairs
            (B) TYPE: nucleic acid
            (C) STRANDEDNESS: unknown
            (D) TOPOLOGY: unknown (ii) MOLECULE TYPE: DNA (genomic)

(iii) HYPOTHETICAL: NO (xi) SEQUENCE DESCRIPTION: SEQ ID NO: 7:

GTGTTTGAAG GTATATCC                                                           18

(2) INFORMATION FOR SEQ ID NO: 8:

(i) SEQUENCE CHARACTERISTICS:
            (A) LENGTH: 21 base pairs
            (B) TYPE: nucleic acid
            (C) STRANDEDNESS: unknown
            (D) TOPOLOGY: unknown (ii) MOLECULE TYPE: DNA (genomic)

(iii) HYPOTHETICAL: NO (xi) SEQUENCE DESCRIPTION: SEQ ID NO: 8:

AATGTCGACA AAGCCACCAT G                                                       21

(2) INFORMATION FOR SEQ ID NO: 9:

(i) SEQUENCE CHARACTERISTICS:
            (A) LENGTH: 17 base pairs
            (B) TYPE: nucleic acid
            (C) STRANDEDNESS: unknown
            (D) TOPOLOGY: unknown (ii) MOLECULE TYPE: DNA (genomic)

(iii) HYPOTHETICAL: NO (xi) SEQUENCE DESCRIPTION: SEQ ID NO: 9:

GTGGCTTTGT CGACATT                                                            17

(2) INFORMATION FOR SEQ ID NO: 10:

(i) SEQUENCE CHARACTERISTICS:
            (A) LENGTH: 29 base pairs
            (B) TYPE: nucleic acid
            (C) STRANDEDNESS: unknown
            (D) TOPOLOGY: unknown (ii) MOLECULE TYPE: DNA (genomic)

(iii) HYPOTHETICAL: NO (xi) SEQUENCE DESCRIPTION: SEQ ID NO: 10:

AATGCGGCCG CGGGGTTTTT GAATGTTCA                                               29

(2) INFORMATION FOR SEQ ID NO: 11:

(i) SEQUENCE CHARACTERISTICS:
        (A) LENGTH: 21 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (xi) SEQUENCE DESCRIPTION: SEQ ID NO: 11:

GTGGCTAGAT ATATTAGGAT C                                      21

(2) INFORMATION FOR SEQ ID NO: 12:

(i) SEQUENCE CHARACTERISTICS:
        (A) LENGTH: 21 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (xi) SEQUENCE DESCRIPTION: SEQ ID NO: 12:

CTGTATTCCT TGCCTGTCCA G                                      21

(2) INFORMATION FOR SEQ ID NO: 13:

(i) SEQUENCE CHARACTERISTICS:
        (A) LENGTH: 21 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (xi) SEQUENCE DESCRIPTION: SEQ ID NO: 13:

TTGCAAGCTG GGATGCAGGC T                                      21

(2) INFORMATION FOR SEQ ID NO: 14:

(i) SEQUENCE CHARACTERISTICS:
        (A) LENGTH: 21 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (xi) SEQUENCE DESCRIPTION: SEQ ID NO: 14:

CTGGACAGGC AAGGAATACA G                                      21

(2) INFORMATION FOR SEQ ID NO: 15:

(i) SEQUENCE CHARACTERISTICS:
        (A) LENGTH: 17 amino acids
        (B) TYPE: amino acid
        (C) STRANDEDNESS: unknown
        (D) TOPOLOGY: unknown (ii) MOLECULE TYPE: peptide -continued (iii) HYPOTHETICAL: NO (xi) SEQUENCE DESCRIPTION: SEQ ID NO: 15:

Ser Cys Pro Glu Glu Pro Gln Leu Arg Met Lys Asn Asn Glu Glu Ala
1               5                   10                  15

Glu (2) INFORMATION FOR SEQ ID NO: 16:

(i) SEQUENCE CHARACTERISTICS:
        (A) LENGTH: 51 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (xi) SEQUENCE DESCRIPTION: SEQ ID NO: 16:

AGCTGTCCAG AGGAACCCCA ACTACGAATG AAAAATAATG AAGAAGCGGA A           51

(2) INFORMATION FOR SEQ ID NO: 17:

(i) SEQUENCE CHARACTERISTICS:
        (A) LENGTH: 17 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (xi) SEQUENCE DESCRIPTION: SEQ ID NO: 17:

Cys Tyr Lys Glu Ser Val Asp Gln Arg Gly Asn Gln Ile Met Ser Asp
1               5                   10                  15

Lys (2) INFORMATION FOR SEQ ID NO: 18:

(i) SEQUENCE CHARACTERISTICS:
        (A) LENGTH: 51 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (xi) SEQUENCE DESCRIPTION: SEQ ID NO: 18:

TGCTACAAAG AATCTGTAGA TCAAAGAGGA AACCAGATAA TGTCAGACAA G           51

(2) INFORMATION FOR SEQ ID NO: 19:

(i) SEQUENCE CHARACTERISTICS:
        (A) LENGTH: 17 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (xi) SEQUENCE DESCRIPTION: SEQ ID NO: 19:

Ile Lys Asn Cys Pro Lys Lys Thr Arg Asn Leu Lys Lys Ile Thr Arg

```
            1               5                  10                  15
Glu (2) INFORMATION FOR SEQ ID NO: 20:

(i) SEQUENCE CHARACTERISTICS:
        (A) LENGTH: 51 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (xi) SEQUENCE DESCRIPTION: SEQ ID NO: 20:

ATTAAAAACT GCCCAAAGAA AACCAGGAAT CTTAAGAAAA TAACTCGTGA G              51

(2) INFORMATION FOR SEQ ID NO: 21:

(i) SEQUENCE CHARACTERISTICS:
        (A) LENGTH: 17 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (xi) SEQUENCE DESCRIPTION: SEQ ID NO: 21:

Cys Lys Ser Arg Ser Leu Asp Arg Arg Gly Ile Gln Arg Ala Ala Asp
1               5                  10                  15
Ile (2) INFORMATION FOR SEQ ID NO: 22:

(i) SEQUENCE CHARACTERISTICS:
        (A) LENGTH: 51 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (xi) SEQUENCE DESCRIPTION: SEQ ID NO: 22:

TGTAAGAGCA GATCCCTGGA CAGGCGAGGA ATACAGAGGG CAGCAGACAT C              51

(2) INFORMATION FOR SEQ ID NO: 23:

(i) SEQUENCE CHARACTERISTICS:
        (A) LENGTH: 17 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (xi) SEQUENCE DESCRIPTION: SEQ ID NO: 23:

Pro Glu Ser Thr Val Met Ala Thr Arg Lys Met His Asp Arg Leu Glu
1               5                  10                  15
Pro
```

(2) INFORMATION FOR SEQ ID NO: 24:

(i) SEQUENCE CHARACTERISTICS:
        (A) LENGTH: 51 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (xi) SEQUENCE DESCRIPTION: SEQ ID NO: 24:

CCAGAATCTA CAGTCATGGC TACACGGAAA ATGCATGATC GTTTAGAACC T            51

(2) INFORMATION FOR SEQ ID NO: 25:

(i) SEQUENCE CHARACTERISTICS:
        (A) LENGTH: 17 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (xi) SEQUENCE DESCRIPTION: SEQ ID NO: 25:

Glu Lys Lys Ser Arg Ser Ser Trp Arg Leu Thr Ser Ser Glu Met Lys
1               5                   10                  15

Lys (2) INFORMATION FOR SEQ ID NO: 26:

(i) SEQUENCE CHARACTERISTICS:
        (A) LENGTH: 51 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (xi) SEQUENCE DESCRIPTION: SEQ ID NO: 26:

GAAAAGAAGT CCCGAAGTTC TTGGAGACTC ACATCCTCAG AAATGAAAAA A            51

(2) INFORMATION FOR SEQ ID NO: 27:

(i) SEQUENCE CHARACTERISTICS:
        (A) LENGTH: 25 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (xi) SEQUENCE DESCRIPTION: SEQ ID NO: 27:

AGCTGTCCAG AGGAACCCCA ACTTC                                         25

(2) INFORMATION FOR SEQ ID NO: 28:

(i) SEQUENCE CHARACTERISTICS:
        (A) LENGTH: 24 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (xi) SEQUENCE DESCRIPTION: SEQ ID NO: 28:

AGCTGTCCAG AGGAACCCCA AGTA                                              24

(2) INFORMATION FOR SEQ ID NO: 29:

(i) SEQUENCE CHARACTERISTICS:
            (A) LENGTH: 21 base pairs
            (B) TYPE: nucleic acid
            (C) STRANDEDNESS: unknown
            (D) TOPOLOGY: unknown (ii) MOLECULE TYPE: DNA (genomic)

(iii) HYPOTHETICAL: NO (xi) SEQUENCE DESCRIPTION: SEQ ID NO: 29:

AGTTTTAGGA TGCTTCTTGG C                                                 21

(2) INFORMATION FOR SEQ ID NO: 30:

(i) SEQUENCE CHARACTERISTICS:
            (A) LENGTH: 24 base pairs
            (B) TYPE: nucleic acid
            (C) STRANDEDNESS: unknown
            (D) TOPOLOGY: unknown (ii) MOLECULE TYPE: DNA (genomic)

(iii) HYPOTHETICAL: NO (xi) SEQUENCE DESCRIPTION: SEQ ID NO: 30:

TGCTACAAAG AATCTGTAGA TCGA                                              24

(2) INFORMATION FOR SEQ ID NO: 31:

(i) SEQUENCE CHARACTERISTICS:
            (A) LENGTH: 18 base pairs
            (B) TYPE: nucleic acid
            (C) STRANDEDNESS: unknown
            (D) TOPOLOGY: unknown (ii) MOLECULE TYPE: DNA (genomic)

(iii) HYPOTHETICAL: NO (xi) SEQUENCE DESCRIPTION: SEQ ID NO: 31:

GTGTTTGAAG GTATATCC                                                     18

(2) INFORMATION FOR SEQ ID NO: 32:

(i) SEQUENCE CHARACTERISTICS:
            (A) LENGTH: 18 base pairs
            (B) TYPE: nucleic acid
            (C) STRANDEDNESS: unknown
            (D) TOPOLOGY: unknown (ii) MOLECULE TYPE: DNA (genomic)

(iii) HYPOTHETICAL: NO (xi) SEQUENCE DESCRIPTION: SEQ ID NO: 32:

AAAAGTACCT GTATTCCT                                                     18

(2) INFORMATION FOR SEQ ID NO: 33:

-continued

```
    (i) SEQUENCE CHARACTERISTICS:
        (A) LENGTH: 19 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (xi) SEQUENCE DESCRIPTION: SEQ ID NO: 33:

AAAAGTACCT GTATTCCTC                                                    19

(2) INFORMATION FOR SEQ ID NO: 34:

(i) SEQUENCE CHARACTERISTICS:
        (A) LENGTH: 19 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (xi) SEQUENCE DESCRIPTION: SEQ ID NO: 34:

AAAAGTACCT GTATTCCTT                                                    19
```

METHOD AND MEANS FOR DETECTING AND TREATING DISORDERS IN THE BLOOD COAGULATION CASCADE

This application claims the benefit of prior filed copending International Application PCT/NL95/00149 having an International filing date of Apr. 21, 1995 which claimed priority for copending European Patent application 94201116.4, filed Apr. 22, 1994.

FIELD OF THE INVENTION

The present invention relates to the field of the detection and/or treatment of (genetic) disorders which lead to defects in the blood coagulation cascade, which may lead to either bleeding disorders or thrombotic disorders. The invention relates specifically to the detection of genetic disorders which lead to said haemostatic disorders and to treatment of said disorders as well as treatment or correction of bleeding tendencies.

BACKGROUND OF THE INVENTION

Maintenance of normal hemostasis requires a delicate balance of the pro- and anti-coagulant mechanisms that are involved in blood coagulation. A dysfunction of one of the proteins may result in bleeding tendencies or thrombotic events. A molecular defect in one of the pro-coagulant proteins is commonly associated with bleeding tendencies, that can be overcome by replacement therapy. This is best illustrated by the bleeding disorder haemophilia A, which is associated with a functional absence of Factor VIII, an essential cofactor in the conversion of Factor X to factor Xa, by activated Factor IX (Kane and Davie. 1988. Blood, vol. 71, 539–555). Diagnosis of bleeding tendencies is performed by simple laboratory tests which are well known in the art. In addition, more specific assays have been developed employing chromogenic substrates in conjunction with purified coagulation Factors that are used to monitor the precise levels of several pro-coagulant proteins. Currently, adequate diagnostic techniques are available to monitor the majority of deficiencies observed in patients with bleeding tendencies.

The anticoagulant pathway, ultimately resulting in the inactivation of the pro-coagulant cofactors V and VIII, by APC, has been described in considerable detail (Esmon, C. T. 1993, Thromb. Haemost. vol. 70, 29–35). Protein S has been implicated as a cofactor in the inactivation of both Factor V and VIII, although the effect of protein S on the catalytic efficiency of cleavage of both Factor V and VIII is relatively small (Koedam et al., 1988, J. Clin. Invest. vol. 82, 1236–1243; Kalafatis and Mann. 1993. J. Biol. Chem., vol. 268, 27246–27257). Functional absence of one of the proteins involved in the anticoagulant pathway is commonly associated with thrombosis. Molecular defects in several proteins involved in the anti-coagulant pathway have found to be associated with thrombotic events. Homozygous protein C deficiency clearly is associated with severe thrombotic events which can be corrected by replacement-therapy (Dreyfus et al., 1991, N. Eng. J. Med. vol. 325, 1565–1568). Heterozygous protein C deficiency has also been established as an increased risk for thrombosis (Bertina et al., 1982, Thromb. Haemost. vol. 48, 1–5), although additional factors seem to be involved in at least some cases (Miletich et al. 1987, N. Eng. J. Med. vol. 317, 991–996). Similar to protein C, protein S deficiency is associated with an increased risk of thrombosis (Comp et al., 1980, J. Clin. Invest. vol. 74, 2082–2088). Relatively rare genetic defects in anti-thrombin III, fibrinogen and plasminogen have also been implicated in thrombosis. Taken together, several deficiencies of proteins involved in the anti-coagulant pathway have been associated with an increased risk of thrombosis. However, the deficiencies outlined above offer an explanation in no more than 10 to 30% of patients suffering from thrombo-embolic disease, while the remainder of the cases remains unexplained (Heijboer et al., 1990, N. Eng. J. Med. 22, 1512–1516). Thus, diagnosis of patients suffering from thrombo-embolic disease is inadequate in 70 to 90% of the cases. Recent advances have decreased the percentage of unexplained thrombosis to 40 to 60%. Dahlbäck and co-workers have observed resistance to APC in a patient suffering from multiple thrombotic events (Dahlbäck et al., 1993, Proc. Natl. Acad. Sci. USA, vol. 90, 1004–1008). An assay based upon the prolongation of the clotting-time by APC, as measured in the activated partial thromboplastin time (APTT) was used to analyze the defect. No prolongation of the APTT upon addition of APC was observed, indicating a defect in the anti-coagulant pathway. Other groups have confirmed the occurrence of APC-resistance in patients suffering from deep vein thrombosis and larger studies performed indicate that 20 to 40% of patients suffering from thrombotic episodes, display resistance to APC (Griffin et al., 1993, Blood, vol. 82, 1989–1993; Koster et al., 1993, Lancet vol., 342, 1503–1506).

The phenotype of APC-resistance is not limited to patients suffering from venous thrombosis. Several studies have documented that the prevalence of APC-resistance is about 2–5% in the normal population. The molecular basis of APC-resistance has remained obscure for some time. A recent study revealed that the phenotype of APC-resistance could be overcome by the addition of purified Factor V to the plasma of affected individuals (Dahlbäck and Hildebrand. 1994. Proc. Natl. Acad. Sci. USA. vol. 91. 1396–1400). Although this observation suggested linkage of APC-resistance to Factor V, no satisfactory explanation was given for the occurrence of resistance to APC at the molecular level.

If the cause or causes for said resistance could be identified, this would lead to a better understanding of thrombolytic disorders, as well as to better detection methods for such disorders and possibly to new and better ways of treatment or prophylaxis of said disorders and other disorders in the blood coagulation cascade.

SUMMARY OF THE INVENTION

The present invention identifies a probable cause for said resistance and gives methods of detection of said causes which methods are simple and result in easy to perform assays.

In one aspect, the present invention provides a method for detecting congenital defects in the anti-coagulant protein C system, comprising the identification of mutations in one or more coagulation factors preventing activated protein C from inactivating said coagulation factors normally under its control. In particular the present invention provides said methods which detect such mutations in Factor V and Factor VIII, especially in cleavage sites for APC in said proteins.

In another aspect the present invention provides mutated Factor V and Factor VIII proteins which have been modified at the cleavage-sites for APC and/or provided with APC resistance.

DESCRIPTION OF THE PREFERRED EMBODIMENTS

Sofar no attention has been directed to the occurrence of mutations at the cleavage-sites for APC in Factor VIII which interfere with inactivation of this pro-coagulant protein.

Figure 2:
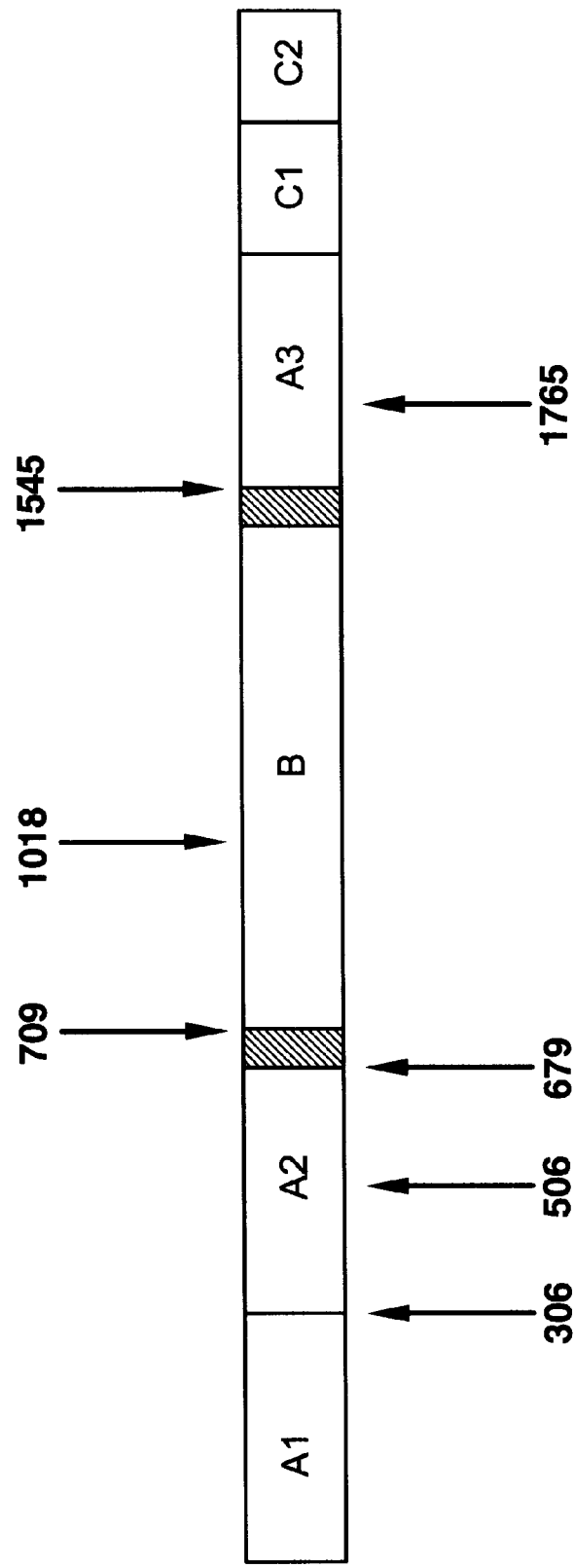
FIG. 2 shows APC cleavage sites for human Factor V.

Studies employing purified proteins have shown that inactivation of Factor VIII occurs through cleavage at the peptide bond $Arg^{562}$-$Gly^{563}$, as well as at the peptide bond $Arg^{336}$-$Met^{337}$. Inactivation of Factor VIII by APC correlates with cleavage at position $Arg^{562}$ (Fay et al., 1991, J. Biol. Chem. vol. 266, 20139–20145). Similar to Factor VIII, the cofactor protein Factor V is also inactivated by APC. Inactivation of Factor V by APC has been described in detail for bovine Factor V (Kalafatis and Mann, 1993, J. Biol. Chem. vol. 268, 27246–27257). Proteolytic inactivation of bovine Factor V by APC occurs at the peptide bonds $Arg^{306}$-$Gln^{307}$, $Arg^{505}$-$Gly^{506}$ and $Arg^{662}$-$Gln^{663}$ of the heavy chain. The light-chain of bovine Factor V is cleaved at the peptide bond $Arg^{1752}$-$Arg^{1753}$ or $Arg^{1753}$-$Ala^{1754}$, although it is unclear whether cleavage at this site is associated with a loss of activity (Kalafatis and Mann, 1993, J. Biol. Chem. vol. 268, 27246–27257). Comparison of the sequences of human and bovine Factor V reveal a considerable homology between the two proteins (Guinto et al., 1992, J. Biol. Chem. vol. 267. 2971–2978). Based upon this homology APC-cleavage-sites have been defined for human Factor V (FIG. 2; see Table I).

Similar to Factor VIII, a mutation at an APC cleavage-site of Factor V results in a prolonged pro-coagulant activity and as such constitutes a potential risk factor for the occurrence of thrombotic events. Sofar, the potential relation between thrombo-embolic disease and genetic defects at APC-sensitive regions in the substrates of APC, have remained unexplored. In view of the high frequency of idiopathic thromboembolic disease, methods to monitor genetic defects at APC-sensitive regions in the substrates of APC clearly are desirable for diagnosis of thromboembolic disease.

A number of the APC cleavage-sites present in both Factor V and Factor VIII have been described and are derived from literature, but the present invention also includes novel cleavage sites for APC in the cofactor proteins Factor V and VIII. Genetic analysis of cleavage-sites for APC in the cofactor proteins V and VIII involves selective amplification of Factor V and VIII DNA-sequences harbouring a cleavage-site for activated protein C and screening of the amplified fragment for the occurrence of mutations. A mutation at an APC-cleavage-site is defined as a deletion or substitution of one or more base-pairs in one the codons that constitute or surround the APC-cleavage-sites of Factors V and VIII. The patient can either be homozygous or heterozygous for the mutation. Selective amplification of Factor V and VIII sequences by RNA-amplification techniques is covered by this invention. Starting material for amplification of Factor V and VIII sequences harbouring a cleavage-site for activated protein C comprises RNA, cDNA derived from RNA by reverse transcriptase activity or genomic DNA. Genomic DNA and RNA are derived from tissue or blood cells of patients and are isolated according to methods that are generally known in the art. Detection of a mutation at the cleavage-sites for APC in Factor V and VIII can be performed by several methods that include but are not limited to:

1. Selective hybridization: An oligonucleotide-primer is designed that selects between RNA, cDNA or genomic DNA that contains a mutation at a cleavage-site for APC and RNA, cDNA or genomic DNA that does not contain a mutation at a cleavage-site for APC. Said oligonucleotide-primer may contain one or more mismatches with respect to the wild-type Factor V and VIII sequence. The wild-type Factor V and VIII sequence are defined as present in the literature including polymorphisms. Detection of the hybrides formed may be carried out according to any one of the many methods available to the man skilled in the art, including but not limited to the use of labelled hybridization probes, which labels can be either direct or indirect, direct meaning labels such as gold sols, radio-isotopes, fluorescent substances and the like; indirect labels including enzymes or through ligand-antiligand interactions such as avidin or streptavidin with biotin, or through the use of antibodies recognizing duplex, etc.

2. Mismatch PCR: Any oligo-nucleotide primer that in conjunction with an another oligo-nucleotide primer selectively amplifies a fragment from RNA, cDNA or genomic DNA that contains a mutation and does not amplify a fragment from RNA, cDNAs or genomic DNA that does not carry a mutation at said cleavage-sites. Also oligo-nucleotide primers designed by persons skilled in the art that selectively amplify a fragment from RNA, cDNA or genomic DNA that do not carry a mutation at said cleavage-sites and do not amplify a fragment from RNA, cDNA or genomic DNA that carry a mutation is included. Said oligonucleotide-primers may contain one or more mismatches with respect to the wild-type Factor V and VIII sequence.

3. PCR-amplification followed by restriction-analysis: This method includes the amplification of a fragment harbouring part of the DNA sequence of Factor V and VIII containing said cleavage-sites followed by digestion with restriction-enzymes that recognize DNA-sequences that are either present in DNA-sequences derived from patients carrying a mutation at said cleavage-sites or that are present in the native Factor V and VIII sequence. In Table II, oligonucleotide primers have been defined that can be used to monitor mutations of this cleavage-sites for APC at amino-acid position $Arg^{506}$ of Factor V and amino-acid position $Arg^{336}$ and $Arg^{562}$ of Factor VIII. Similar strategies can be devised for the occurrence of mutations at amino-acid position $Arg^{306}$, $Arg^{679}$ and $Arg^{1765}$ of Factor V and other cleavage-sites for APC.

4. Sequencing analysis: This method includes direct analysis of the DNA sequence surrounding and constituting said cleavage-sites. This method involves any protocol that is currently available or will be available to any person skilled in the art, for directly determining the DNA- or RNA :sequence that encodes said cleavage-sites.

Other methods that discriminate between RNA, cDNA or genomic DNA that contains a mutation at said cleavage-sites for APC and RNA, cDNA or genomic DNA that does not contain a mutation at a cleavage-site for APC, may be identified by the average expert in the art. Such variations leading to the selective detection of alterations at said cleavage-sites are to be considered as belonging to the present invention.

Example 1 provides details on the detection of mutations at amino-acid position $Arg^{506}$ of Factor V and illustrates the general use of the methods for the detection of mutations at cleavage-sites of APC as disclosed in this invention. The knowledge that the mutant factors exist can of course also be exploited therapeutically. Now that the reason why certain patients have a higher risk for suffering from thrombosis has been identified and can be detected according to the invention, it is of course clear that the defect can be corrected by either providing normal factors to the patient in which the defect has been detected, or to provide the patient with the correct factors by means of gene therapy, providing the patient with normal factors as well (preferably through site-directed homologous recombination).

On the other hand now that the mutation, or rather the site of mutation, which leads to APC resistance has been identified, it has become possible to use said mutants as therapeutic agents as well, although maybe not directly in thrombotic disorders, but very definitely in the field of bleeding disorders.

Treatment of bleeding disorders is usually performed by replacement-therapy with preparations that consist of (partially) purified clotting factors. The most common bleeding disorder is Haemophilia A which is a result of functional absence of Factor VIII. Treatment of patients suffering from Haemophilia A has evolved dramatically during the past years. Initially, cryoprecipitate containing Factor VIII has been used for treatment of Haemophilia A patients. Intermediate-purity concentrates obtained by partial purification of Factor VIII from cryoprecipitate constitute an improvement of therapy. A further improvement is provided by the use of monoclonal antibodies directed at Factor VIII and von Willebrand factor to obtain Factor VIII-preparations that consist almost exclusively of Factor VIII (Hoyer, L. W., 1994, N. Eng. J. Med. Vol.330, 38–47). Recently, recombinant Factor VIII obtained from animal cells in which the Factor VIII cDNA has been introduced have become available for treatment. Recombinant DNA technology provides the opportunity to produce unlimited amounts of Factor VIII. Furthermore, recombinant DNA technology enables us to optimize the functional properties of Factor VIII thereby improving treatment of patients suffering from Haemophilia A. According to the invention we can now provide Factor VIII and Factor V derived proteins, which are more resistant to APC than wild-type Factor VIII and V. According to the invention there is provided a Factor VIII-protein which is resistant to inactivation by APC, preferably as a result of modification of the APC-cleavage-site at amino-acid position $Arg^{336}$ and/or $Arg^{562}$ of Factor VIII. These kind of proteins are arrived at by construction of a Factor VIII CDNA in which for instance the codon encoding $Arg^{562}$ has been replaced by an Ile encoding codon by using techniques that are known to a person skilled in the art. Such a factor VIII encoding cDNA harbouring the $Arg^{562}$ to Ile mutation may of course contain additional modifications that include for instance deletion of a large part of the B-domain Mertens et al., 1993. Br. J. Haematol. vol. 85, 133–142). Expression of the modified factor VIII cDNA in eukaryotic of prokayotic cells can be carried out according to methods known to persons skilled in the art. Alternatively, the modified Factor VIII cDNA may be expressed in transgenic animals or introduced in a retroviral vector that can be used in gene-therapy protocols. Also included are alternative methods that may result in therapeutically useful Factor VIII-protein modified at at least one of its cleavage-sites for APC. Purification of said proteins may occur by monoclonal antibody technology or other methods that are available to persons skilled in the art. Furthermore, said pharmaceutically useful proteins consisting of factor VIII modified at their APC-cleavage-sites may be purified by other methods that are known to persons skilled in the art.

Despite the fact that considerable progress has been made over the last 20 years in treatment of patients with Haemophilia A, one of the major problems associated with Factor VIII replacement-therapy remains unsolved. In about 5 to 20% of the Haemophilia A patients treated with factor VIII, antibodies that inhibit factor VIII-activity develop (Ehrenforth et al., 1992, Lancet, vol. 339, 594–598). These so-called Factor VIII-inhibitors usually arise at 5 to 20 exposure-days to Factor VIII and can provide serious clinical complications (Aledort, L. 1994. Am. J. of Haemat. vol. 47, 208–217). Inspection of the incidence of Factor VIII-inhibitors in patients treated with different Factor VIII containing pharmaceutical preparations, reveals no gross differences. These observations suggest that development of Factor VIII-inhibitors is usually not related to the Factor VIII-preparations administered. Several protocols have been established for the treatment of inhibitors in Haemophilia A patients. Low or moderate levels of inhibitors are usually treated by administration of high doses of Factor VIII (Hoyer, L. W. 1994. N. Eng. J. Med. vol. 330. 38–47). In addition some Haemophilia A patients who developed an inhibitor have been succesfully treated with Factor VIII isolated from porcine plasma (Hay et al., 1990. Blood. vol. 76, 882–886). The latter treatment is associated with a risk of inhibitor-development against porcine Factor VIII and indeed this has been reported for several Haemophilia A patients who were treated with preparations containing porcine Factor VIII. Extracorporeal adsorption of inhibiting antibodies to Factor VIII by Protein-A-Sepharose has been employed in Haemophilia A patients with high levels of Factor VIII-inhibitors (Nilsson et al., 1988, N.Eng. J. Med. vol. 318, 947–950). This treatment requires specialized equipment and has been reported to be succesful in 9 out of 11 patients with a high level of Factor VIII-inhibitors. The different treatments described have met with variable success and it is clear that additional methods of treatment may be useful for the treatment of Haemophilia A patients with inhibitors.

A general established option for the treatment of Haemophilia A patients with an inhibitor is provided by administration of so-called "Factor VIII bypassing acgents". Initially prothrombin-complex concentrates (PCC) and activated prothrombin complexes concentrates (APCC) have been used in Haemophilia A-patients with an inhibitor (Lusher et al., 1980, N. Eng. J. Med. vol. 303, 421–425; Sjamsoedin et al., 1981, N. Eng. J. Med. vol. 305, 717–721). Treatment with PCC was considered only partially effective and was associated with myocardial infarction and disseminated intravascular coagulation in some of the patients treated. APCC is considered to be more effective compared to PCC although administration of activated clotting factors present in PCC may give rise thrombogenicity as evidenced by the increased fibrinopeptide A levels observed in patients treated with APCC. Activated Factor VII has been used for treatment of Haemophilia A patients with inhibitors (Hedner, U and W. Kisiel, 1983. J. Clin. Invest. 71, 1836–1841; Hedner et al., 1988, Lancet, 309, 1193). Furthermore, both Tissue-Factor and a mixture of Factor Xa and phospholipids have been used succesfully in canine models of Factor VIII-deficiency (O'Brien et al., 1988. J. Clin. Invest. vol. 82, 206–211; Giles et al., 1988. Brit. J. Haematol. vol. 69, 491–497). At this moment the efficacy of Factor VIIa, Tissue Factor and a combination of Factor Xa and phospholipids as "Factor VIII bypassing agent" is not clear. Furthermore, both PCC and APCC do not provide an adequate treatment in about 30 to 50% of the cases. Clearly, a need exists for additional pharmaceutical preparations that can be used as Factor VIII bypassing agent.

The present invention provides Factor VIII bypassing agents, which are based on the proteins that have been implicated as a risk factor in thrombosis according to the present invention. These proteins include but are not limited to Factor V proteins modified at a cleavage-site for APC so as to induce APC resistance of said proteins, or fragments or derivatives of such proteins having comparable biological activity (in kind, not especially in amount).

Assays as described previously in this application may be used to identify material that contains cofactor-molecules Factor V and VIII which have been modified at the cleavage-sites for APC. Following identification of such plasma derived from patients having these mutated proteins, preparations that contain fixed amounts of the hypercoagulant cofactor-proteins can be produced. Alternatively, proteins modified at their APC-cleavage-sites may be obtained through recombinant DNA technology involving expression of the modified proteins in eukaryotic or prokayotic cells and/or transgenic animals. Also therapeutic use of a Factor V protein modified at the( APC-cleavage-site of $Arg^{506}$ or any other APC-cleavage-sites by methods that involve gene-therapy protocols, that include but are not limited to the use of a retroviral vector, are included. Purification of said proteins may occur by monoclonal antibody technology, plasma fractionation methods or any other method that is available to persons skilled in the art. Furthermore, said pharmaceutically useful proteins consisting of Factor V proteins modified at their APC-cleavage-site may be purified from a mixture of proteins containing also non-modified Factor V. Purification may involve monoclonal antibodies that specifically recognize Factor V that has been modified at one or more of the cleavage-sites for APC or purification by other methods that are known to persons skilled in the art.

Factor V-proteins modified at amino-acid position $Arg^{306}$ and/or $Arg^{506}$ and/or $Arg^{679}$. The arginine-residue that preceed the APC-cleavage-site can be changed into a Gln, Ile or any other amino-acid. Therapeutic use of Factor V containing the amino-acid substitution $Arg^{506}$-Gln or other modifications of APC-cleavage-sites will be useful for the treatment of Haemophilia A patients with inhibitors. Based upon the ability of Factor V containing the amino-acid substitution $Arg^{506}$-Gln to promote thrombus-formation as observed in patient, with venous thrombosis, this protein will be useful as “Factor VIII bypassing agent”. In view of the limited effectiveness and high costs of current treatment of Haemophilia A patients with inhibitors pharmaceutical preparations that contain said Factor V will prove to be more effective. The therapeutic preparation may consist of purified Factor V containing the amino-acid substition $Arg^{506}$-Gln. Alternatively, said modified Factor V may be a component of a therapeutic preparation. Said preparation may be any therapeutic preparation derived from plasma, such as prothrombin complex concentrate (PCC) or activated prothrombin complex concentrates (APCC).

In summary the invention provides means and methods for detecting certain thrombotic disordes and by identifying the cause of such disorders, i.e. APC resistance, it also provides means for correcting said disorders, for instance through gene therapy. On the other hand it also provides therapeutic agents for the treatment of the opposite kind of disorders, being bleeding disorders, in that the mutated Factors V and VIII which have APC resistance can be used for their hyper pro-coagulation activity. It will be clear that the invention extends to derivatives and/or fragments of such therapeutic agents, no matter how they have been obtained. The person skilled in the art knows how to determine the dose of therapeutic agent to be administered to a patient, said dose being dependent on numeral factors such as degree of the disorder, bodyweight of the patient to be treated, specific activity of the chosen therapeutic agent, etc. If not directly clear to the skilled artisan, the dose can be arrived at by methods well known in the art, in particular through so called dose finding studies, which involve administering to animals such as rodents and later to (healthy) volunteers rising doses of the chosen therapeutic agent. In general the close to be given to a human will lie between 1 and 500, more preferably 5–50 units per kg of body weight per day. Pharmaceutical formulations in which the agents according to the invention can be administered are well known in the art. The agents are protein-like materials, therefor formulations which are known to be suitable for proteins will be suitable for the agents of the invention.

They may be given alone or together with other therapeutic agents. They may even be given together with normal Factor VIII and/or V in order to delicately balance the amount of coagulant activity given.

The invention will be illustrated in more detail in the following examples.

EXAMPLE 1

Identification of mutations at the cleavage-site for activated protein C at amino-acid position $Arg^{506}$ of factor V in patients suffering from venous thrombo-embolism.

Twenty-seven patients with (recurrent) idiopathic episodes of thromboembolism confirmed by contrast venography and/or pulmonary angiography were investigated for the occurrence of mutations at amino-acid position $Arg^{506}$ of factor V. None of the patients analyzed had an acquired or inherited deficiency of antithrombin III, protein C, protein S or of plasminogen. Routine screening of blood coagulation and fibrinolysis revealed no abnormality. Peripheral blood lymfocytes were isolated from blood by Ficoll-Paque densitygradient centrifugation. RNA was isolated from peripheral blood lymphocytes using the RNAzol B method (WAK Chemie, Bad Homburg v.d.H., Germany) and cDNA was prepared essentially as described previously (Cuypers, et al. 1992, J. Clin. Microbiol. vol.30, 3220–3224). Patients were analyzed for the presence of mutations at amino-acid position $Arg^{506}$ of factor V, using the following oligo-nucleotide primers: 5' TGTAAGAGCAGATCCCTGGACTCG 3' (primer 506-1; sense; nucleotide 1576–1600 of human factor V, SEQ ID NO: 1 nucleotide 1 corresponds to the first nucleotide of the start-codon of factor V); 5' CATCACGTTTCACCTCATCAGG 3' (primer 506-2; antisense; nucleotide 1708–1730 of human factor V) SEQ ID NO:2. Oligonucleotide-primer 506-1 contains two mismatches with respect to the native factor V sequence which are underlined. The two mismatches together with the adjacent CGA codon, coding for $Arg^{506}$ introduce a restriction-site for the restriction-enzyme NruI upon amplification with oligonucleotide primers 506-1 and 506-2 (see Table II). Amplification by PCR employing oligonucleotide-primer 506-1 and 506-2, of cDNA isolated from several patients suffering from venous thrombo-embolism yielded a fragment of 154 base pairs (bp), which encodes the part of factor V that contains the APC cleavage-site at amino-acid position $Arg^{506}$. The occurrence of mutations at amino-acid position $Arg^{506}$ was monitored by digestion of the amplified fragments by the restriction-enzyme NruI.

In FIG. 3, lane 2, an amplified fragment which can be digested by NruI is shown, yielding a fragment of 130 bp.

Figure 3:
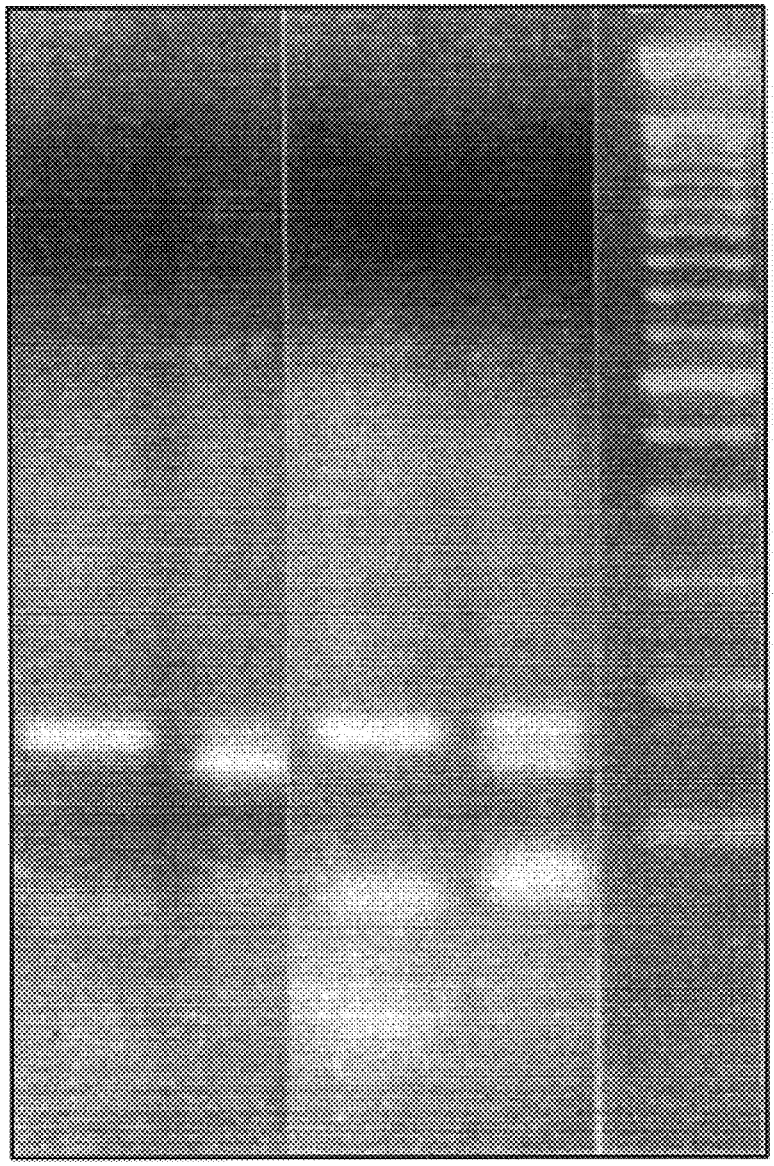
FIG. 3 shows results of Example 1.
Figure 4:
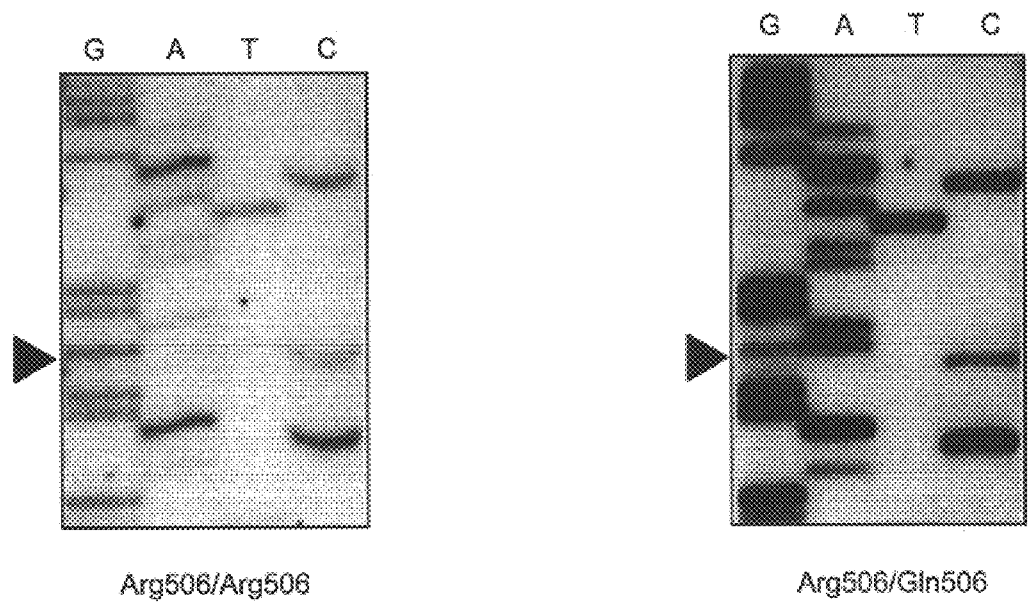
FIG. 4 shows additional results of Example 1.

Since NruI is able to digest the amplified PCR-fragment, no mutation at amino-acid Arg$^{506}$ is present in this individual (individual A). In FIG. 3, lane 4, an amplified fragment is shown that is partially digested by NruI, indicating the presence of a mutation at amino-acid position Arg$^{506}$ in one of the alleles of factor V of this individual (individual B). In order to confirm the presence of a mutation at amino-acid position Arg$^{506}$ in individual B, the following strategy was employed. Oligonucleotide-primers were designed in order to amplify a larger portion of the factor V CDNA; S' ATCAGAGCAGTTCAACCAGGG 3' (primer 506-5; sense, nucleotide 1414–1435 of human factor V) SEQ ID NO: 3 and 5' CATCACGTTTCACCTCATCAGG 3' (primer 506-2 antisense; nucleotide 1708–1730 of human factor V)SEQ ID NO:2. Amplification by PCR with primers 506-2 and 506-5 yielded a fragment of 316 base pairs (bp), which encodes the part of factor V that contains the APC cleavage-site at amino-acid position Arg$^{506}$. The occurrence of mutations at amino-acid position Arg$^{506}$ was monitored by direct sequencing of the amplified fragment (FIG. 4). Clearly, in individual B a mutation is present within the codon Arg$^{506}$; since at the second base pair of this codon both a "G" and an "A" are observed, resulting in a substitution of Arg$^{506}$ (CGA) for a Gln (CAA) in one of the alleles of the gene for factor V in individual B. Direct sequencing was also employed for an individual A, which did not reveal an abnormal restriction-pattern upon digestion of the 154 bp fragment resulting from amplification with oligonucleotide-primers 506-1 and 506-2 (see FIG. 3; lane 2). Direct sequencing of individual A did not reveal mutations at amino-acid position Arg$^{506}$ of factor V (FIG. 4; left panel). These results clearly show that the different assays employed here are capable of detecting mutations at amino-acid position Arg$^{506}$ of human factor V.

Next, we analyzed all 27 patients with documented idiopathic (recurrent) thromboembolism for the occurrence of point mutations within the activated protein C (APC) sensitive regions of blood coagulation factor V. Employing amplification with oligonucleotide-primers 506-1 and 506-2, followed by NruI digestion as well as direct sequencing of amplified fragments, 10 of these patients revealed a single G to A transition and appeared to be heterozygous for the Arg$^{506}$ to Gln$^{506}$ mutation. The methods described are capable of defining the molecular defect in approx. 35% of the patients suffering from thromboembolic disease which could not be diagnosed prior to the availability of the methods described in this invention.

The results obtained indicate that monitoring of the occurrence of mutations at the APC-cleavage-site of factor V in patients suffering from thromboembolic disease, constitute a major breakthrough in the diagnosis of idiopathic thromboembolism.

As described in the previous paragraph 10 individuals have been found that are heterozygous for the Arg$^{506}$ to Gln mutation. Sequencing analysis revealed that in all cases examined a single nucleotide "GI to "A" substitution was present.

An assay was developed to monitor for the presence of this single base-pair substitution, based upon oligonucleotide primers depicted in Table III. Genomic DNA of all patients studied was isolated employing standard procedures. Amplification by PCR with oligonucleotide-primers 506-5 and 506-6 yields a fragment of 206 bp in patients examined. PCR-amplification with oligonucleotide-primers 506-5 and 506-7 yields a 206 bp fragment in all patients examined. Finally PCR-amplification with oligonucleotide-primers 506-5 and 506-8, specific for the Arg$^{506}$ to Gln substitution, solely yields a fragment of 206 bp in the 10 patients that are heterozygous for the Arg$^{506}$ to Gln substitution. No product is observed following PCR amplification with these oligonucleotide-primers in the patients that do not carry the Arg$^{506}$ to Gln mutation.

In conclusion, several methods have been described capable of diagnosis of mutations at amino-acid position Arg$^{506}$ of factor V. Applicability of these methods to patients suffering from thrombo-embolic disease clearly indicate the utility of these assays in diagnosis of thrombo-embolic disease.

EXAMPLE 2

Thrombin generation in plasma containing factor V with or without mutation at a cleavage site for activated protein C.

Figure 5:
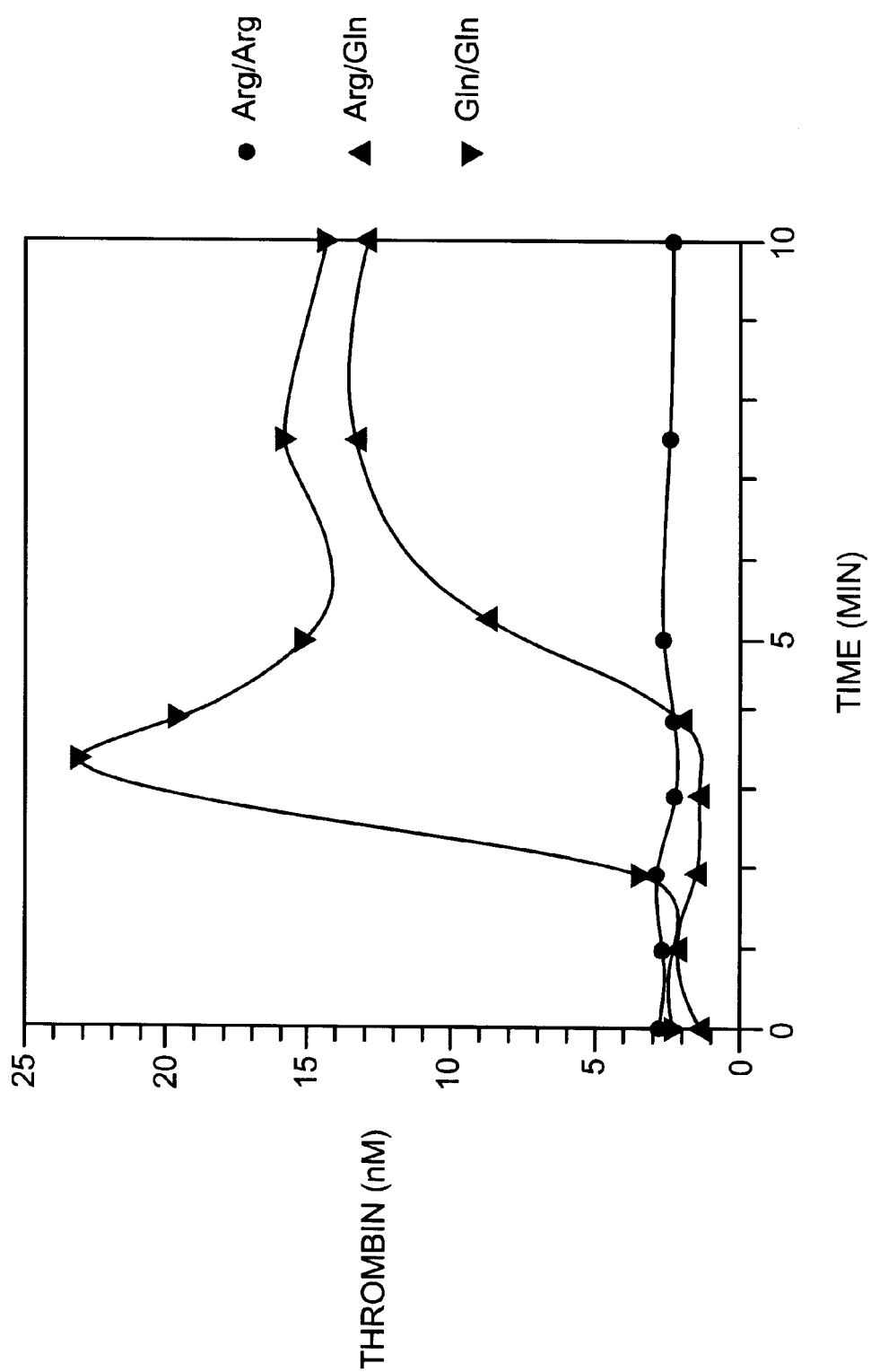
FIG. 5 is a graph showing results of Example 2.

The utility of the methods described in Example 1 is not limited to the diagnosis of patients suffering from thrombo-embolic disease, but also includes the assessment of the pro-coagulant potential of plasma from healthy blood donors. To evaluate the balance between pro-coagulant and anti-coagulant pathways, a simple test method was developed. This was based on the generation of the pro-coagulant thrombin in the presence of an excess of the anti-coagulant activated protein C. This assay was performed as follows. First, 50 μl of citrated, platelet-poor plasma were added to a plastic test tube containing 350 μl of a dilution buffer of 50 mM Tris (pH 7.3) and 0.1% (w/v) bovine serum albumin (Sigma Chemical Co., St. Louis, U.S.A.). Then 400 μl of APTT reagent (Chromogenix AB, Mölndal, Sweden) were added as the source of phospholipids and colloidal silica to activate the coagulation system. After incubating this mixture for 5 min at 37° C., 400 μl were added of a pre-warmed mixture of the Tris/albumin dilution buffer containing 25 mM CaCl$_2$ and 1 μg/ml of purified human activated protein C (Kisiel, 1979, J. Clin. Invest. vol 64, 761–769). With regular intervals, 45 μl samples were drawn. These were immediately mixed with 5 μl of 0.25 M EDTA to stop further thrombin formation. Subsequently, samples were diluted 5 to 20-fold in Tris/albumin buffer, and mixed with an aqueous solution (1.0 mM final concentration) of the chromogenic substrate S2238 (Chromogenix AB, Mölndal, Sweden). The absorbance at 405 nm then was monitored spectrophotometrically. The assay was calibrated with purified human thrombin (Mertens et al., 1985, Thromb. Haemostasis vol. 54, 654–660) in order to convert rates of absorbance increase into molar concentrations of thrombin. FIG. 5 shows the thrombin generation in this assay using plasma samples from three distinct blood donors, of which the factor V genotype had been established as Arg$^{506}$/Arg$^{506}$, Arg$^{506}$/Gln$^{506}$ and Gln$^{506}$/Gln$^{506}$ by using the PCR technique described in Example 1. As is evident from FIG. 5, thrombin formation in this assay system was completely dependent on the presence of the Arg to Gln mutation at amino-acid position 506 of factor V. Moreover, the extent of thrombin formation clearly distinguished between plasma from donors which are homozygous and heterozygous for this mutation. These data demonstrate that factor V which carries a mutation at a cleavage site for activated protein C is an unusually powerful pro-coagulant which greatly contributes to the overall pro-coagulant potential of human plasma.

EXAMPLE 3

Preparation of a factor V-containing fraction from human blood plasma.

In current plasma fractionation schemes, no specific steps have been implemented to prepare fractions that are deliberately enriched in factor V. Methods for the purification of factor V from plasma have been well established, both by conventional precipitation and chromatographic techniques (Suzuki et al., 1982, J. Biol. Chem. vol. 257, 6556–6564) and by immuno-affinity chromatography (Katzmann et al., 1981, Proc. Natl. Acad. Sci. U.S.A. vol. 78, 162–166). On industrial scale, however, the utility of these methods is limited because they would produce factor V at the expense of urgently demanded products such as factor VIII and immunoglobulins.

As factor V isolation preferably should be compatible with regular plasma fractionation schemes, various regular plasma fractions were evaluated as potential sources of factor V. Fractions were analysed for factor V activity using the classical one-stage clotting assay (Biggs, 1976, Human blood coagulation, haemostasis and thrombosis, 2nd edition, Blackwell, Oxford, pp. 310–364), using commercially obtained factor V deficient plasma (Baxter, Düdingen, Switzerland) and human tissue thrombopastin (Thromborel$^R$-S, Behring, Marburg, Germany). The fractionation process examined comprised cryoprecipitation and anion exchange steps prior to the common ethanol fractionation for albumin and immunoglobulin (Brummelhuis, in: Methods of plasma protein fractionation (J. M. Curling, Ed.), 1980, Academic Press, London, pp. 117–128). Analysis of six different fractionation runs demonstrated that in the first step, about 80% of the initial factor V activity was recovered in the cryosupernatant plasma. In the second step, a substantial amount (at least 50%) of the factor V activity proved to be adsorbed to the anion exchange resin DEAE-Sephadex A-50 (Pharmacia, Uppsala, Sweden) used for the preparation of Prothrombin Complex Concentrate (PCC). After washing and elution as described (Brummelhuis, vide supra), the resulting PCC was found to contain varying concentrations (between 5 and 20%) of the initial factor V activity. Small scale experiments, employing 10 ml portions of cryosupernatant plasma, demonstrated that factor V yields could be improved by (1) increasing the amount of DEAE-Sephadex to at least 1.5 g per kg of cryosupernatant plasma, (2) lowering the ionic strength during the adsoption stage by diluting the cryosupernatant plasma, (3) lowering the ionic strength of the washing conditions before elution, or (4) by a combination of these improvements.

By using an improved process for the preparation of PCC, it appeared feasible to obtain up to 30% of the initial factor V in this plasma fraction. Assessment of purity of this fraction by assaying factor V activity and protein content (Bradford, 1976, Anal. Biochem. vol 72, 248–254) revealed a specific activity of 0.4 units/mg, which corresponds with a 25-fold purification. Thus, an improved process ot PCC preparation provides access to a factor V-enriched plasma fraction without interfering with the preparation of factor VIII, albumin, or immunoglobulin products. This partially purified factor V then may serve as the source material for further purification by the above-referenced conventional or immuno-affinity methods to the desired degree of purity.

EXAMPLE 4

Thrombin generation in factor V-containing fractions prepared from source plasma selected for Arg or Gln at factor V position 506.

For the preparation of partially purified factor V, blood was collected in citrate-containing standard anticoagulants. Cells were collected by centriguation (15 min at 5,000 g), and the supernatant plasma was frozen and stored below −30° C. until use. Individual plasma samples were screened by the method described in Example 2, and divided into the three (categories, according to the phenotype as apparent from the thrombin generation profiles (cf. FIG. 5). In all cases, peripheral blood lymfocytes of the same donors were isolated to confirm the genotype by PCR analysis as described in Example 1. Plasma then was thawed at 4° C., and the cryoprecipitate was collected by centrifugation (5 min at 2,000 g). Cryosupernatarnt plasmas of the same phenotype were pooled, and DEAE-Sephadex A-50 (Pharmacia, Uppsala, Sweden) was added in an amount of 1.5 g dry weight per kg of plasma. The mixture was stirred for 30 min at room temperature, and transferred to a column to collect the anion exchange resin. The column was washed using a buffer of 10 mM Tri-sodium citrate (pH 7.0) containing 154 mM NaCl, and the factor V-enriched PCC-fraction was eluted with the same buffer containing 0.7 M NaCl. This process yielded three distinct PCC-fractions, containing the factor V types $Arg^{506}$, $Gln^{506}$ or, from the heterozygous donors, a mixture of these two.

Figure 6:
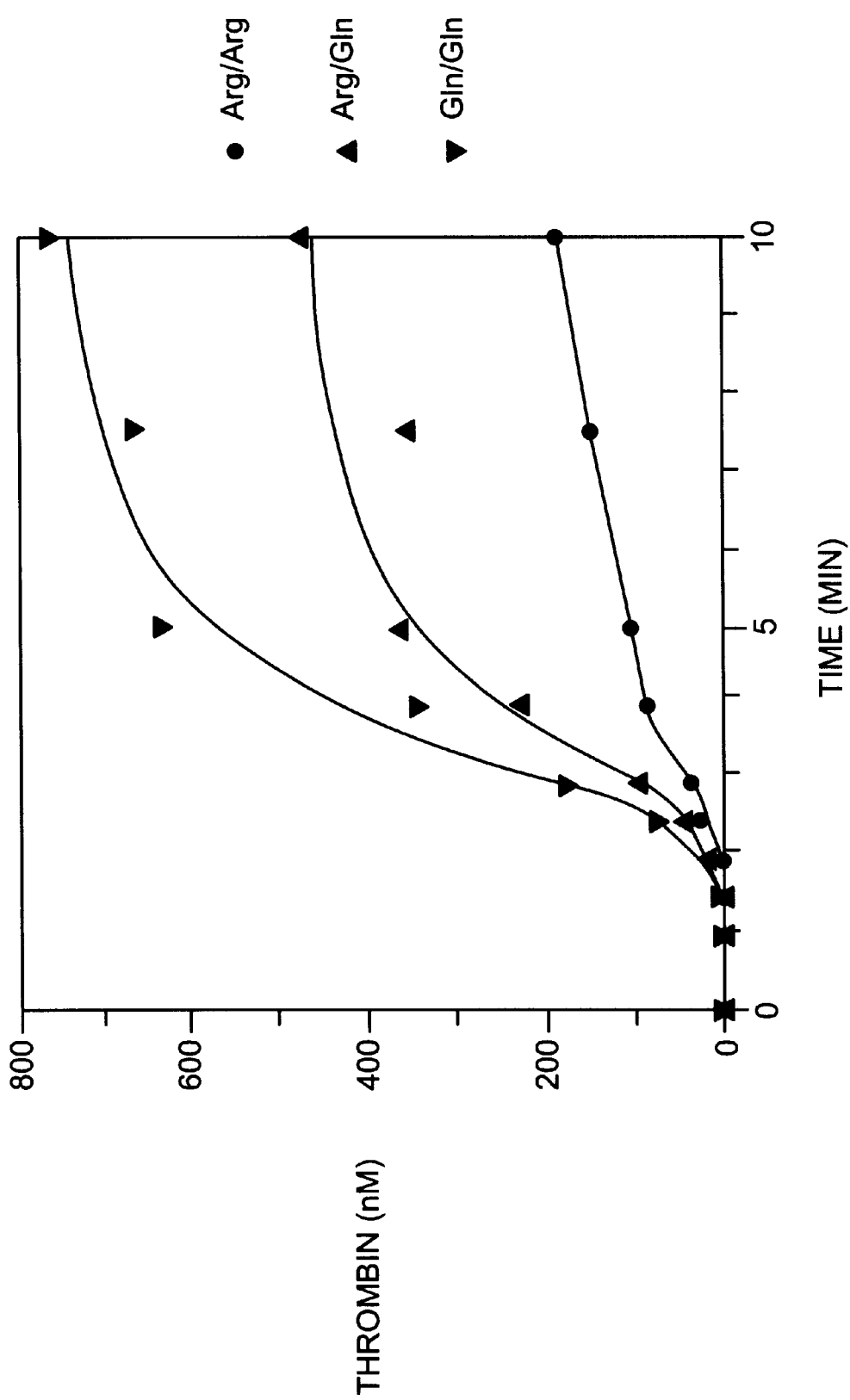
FIG. 6 is a graph showing results of Example 4.

For assessment of the thrombin generating potential of the three PCC fractions, PCC was diluted to a factor V activity of between 0.2 and 0.3 units/ml in a buffer containing 50 mM Tris (pH 7.3) and 0.1% (w/v) bovine serum albumin. Then thrombin generation was assessed by the same method as described in detail in Example 2, using 400 $\mu$l of diluted PCC, 400 $\mu$l of APTT reagent, and 400 $\mu$l of Tris/albumin buffer containing 25 mM $CaCl_2$, 1 $\mu$g/ml of purified human activated protein C, and ½₀₀₀-diluted thromboplastin reagent (Tromborel$^R$, Behring, Marburg, Germany) to further activate the coagulation system. With regular intervals, samples were drawn for the quantification of thrombin employing the method described in Example 2, and the thrombin generation profiles were constructed (see FIG. 6). As is evident from FIG. 6, thrombin formation was greatly dependent on the presence of the Arg to Gln mutation at amino-acid position 506 of factor V. Moreover, the extent of thrombin formation clearly distinguished between PCC from donors which are homozygous and heterozygous for the mutation.

These data demonstrate that the powerful pro-coagulant effect of factor V which carries a mutation at a cleavage site for activated protein C is not restricted to full plasma, but is equally manifest in factor V-enriched plasma fractions such as PCC. Screening of source plasma for said mutations as the first step in the preparation of factor V-containing plasma fractions thus leads to pharmaceutical preparations that greatly differ with respect to thrombin generation in the presence of activated protein C. As is evident from FIG. 6, this finding is advantageous in reducing the pro-coagulant potential of PCC, which decreases the currently known thrombogenic potential of PCC, or in enhancing its pro-coagulant potential, as is desirable for improving the efficacy of PCC in the treatment of patients with inhibitory antibodies against factor VIII or other coagulation factors.

EXAMPLE 5

Figure 7:
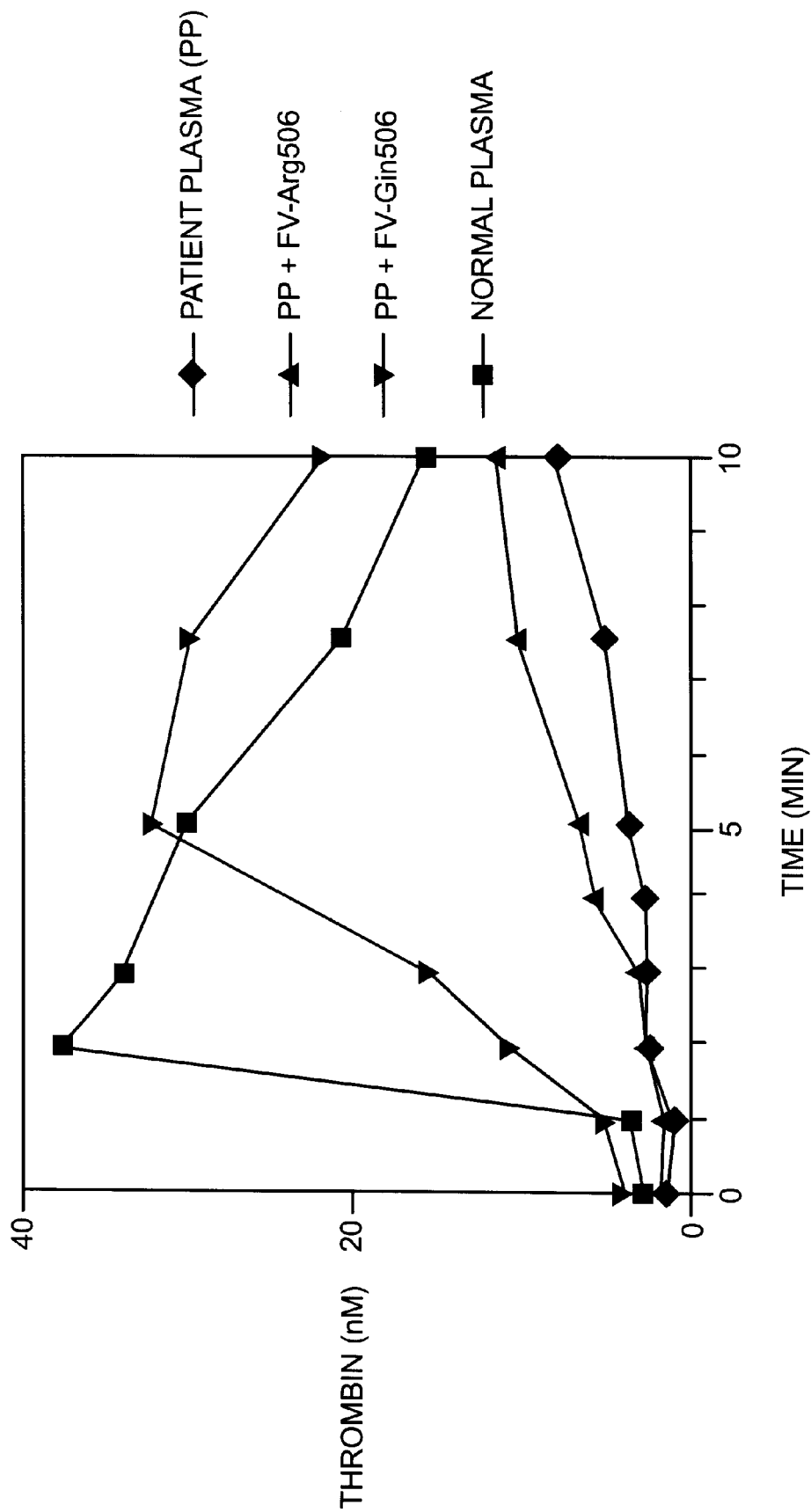
FIG. 7 is a graph showing result of Example 5.

Factor V with a mutation at a cleavage site for activated protein C displays factor VIII inhibitor bypassing activity Plasma was collected from a patient with severe haemophilia A and an inhibitor against factor VIII. His anti-factor VIII titer was determined employing the so-called 'Bethesda assay' (Kasper et al., 1975, Thromb. Diath, Haemorrh. vol 34, 869–872), and found to be 40 Bethesda Units. As such, this high titer is prohibitive for the normal substitution therapy with factor VIII. 100 $\mu$l of the patient's plasma were supplied with partially purified factor V to a final concentration of 0.5 units/ml. This factor V was purified from plasma that had been selected for the presence of the Arg to Gln mutation at amino-acid position 506 as described in detail in Example 4. The mixture then was diluted to 400 μl using a buffer containing 50 mM Tris (pH 7.3) and 0.1% (w/v) bovine serum albumin. Then thrombin generation was assessed by the same method as described in detail in Example 2, using 400 μl of APTT reagent, and 400 μl of Tris/albumin buffer containing 25 mM and ⅛₀₀₀-diluted thromboplastin reagent (see Example 4). With regular intervals, samples were drawn for the quantification of thrombin employing the method described in Example 2, and the thrombin generation profiles were constructed (see FIG. 7). As is evident from FIG. 7, only minor thrombin formation was detected in the absence of added factor V or after the addition of factor V with Arg at amino acid position 506. In the presence factor V with the Arg to Gln mutation at amino-acid position 506, however, thrombin formation appeared to be similar to that in normal non-haemophilie plasma. This demonstrates that a pharmaceutical preparation comprising the factor V Arg$^{506}$->Gln variant displays factor VIII bypassing activity, and as such has utility in correcting a coagulation defect.

EXAMPLE 6

Construction of a Factor VIII molecule with a mutation at a cleavage site for activated protein C.

Figure 1:
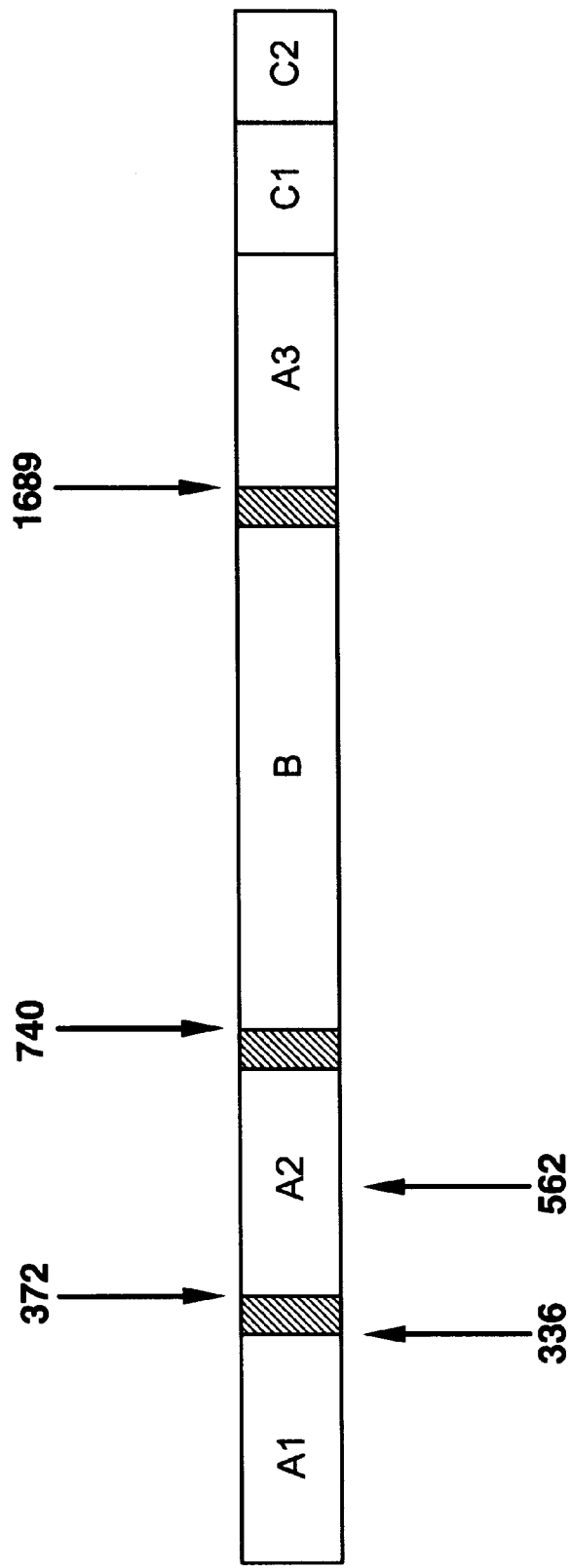
FIG. 1 shows the activation and inactivation sites for respectively thrombin and APC in Factor VIII.

As shown in Examples 2 and 4, cofactor molecules with a mutation at a cleavage site for activated protein C may occur in plasma of normal, healthy blood donors, and the variant cofactor can be selectively obtained by screening of donor plasmas before purification. Access to such variants may be restricted according to their prevalence in the normal donor population. This limitation can be overcome by producing such variants by recombinant DNA technology. An example of this strategy is provided by the following description, which outlines the construction and expression of a Factor VIII cDNA containing a substitution at the cleavage site Arg$^{562}$ for activated protein C. This description is exemplary to an average expert in the art for the creation of similar substitutions at other cleavage sites in the cofactor molecule factor VIII (see FIG. 1).

Previously, we have described the plasmid pCLB-BPVdB695 which encodes a B-domain-deleted form of Factor VIII cDNA (Mertens et al., Br. J. Haematol. vol. 85, 133–142). We have employed the polymerase chain reaction to prepare a factor VIII cDNA in which Arg$^{562}$ has been substituted for Ile. A 1206 bp fragment was amplified using plasmid pCLB-BPVdB695 as a template employing the following oligonucleotide-primers: F8-547S 5' CTGG-TAAAAGACTTGAAT 3' (nucleotide 547–565 of the Factor VIII cDNA) SEQ ID NO:4; sense and F8-1732AS 5' CTG-GTTTCCATTTTGATCTAC 3' (nucleotide 1732–1753 of Factor VIII cDNA; antisense mismatches are underlined) SEQ ID NO:5. In addition a 306 bp fragment was amplified using plasmid pCLB-BPVdB695 as a template with the following oligonucleotide-primers: F8–1732S 5' GTAGAT-CAAAATGGAAACCAG 3' (nucleotide 1732–1753 of Factor VIII; sense mismatches are underlined) SEQ ID NO:6 and F8–2020AS 5' GTGTTTGAAGGTATATCC 3' (nucleotide 2020–2038 of Factor VIII) SEQ ID NO:7; antisense. Reaction conditions were: 2' 90° C., 20' 50° C., 3' 72° C.; 37 times 45" 90° C., 90" 50° C., 3" 72° C.; 5' 65° C. in the presence of 1 mM dNTPs, 10 times Pfu-polymerase reaction buffer, 50 pMol of primer H1 and H2 and 2.5 U of Pfu-polymerase (Stratagene, Cambridge, UK). The 306 bp fragment and the 1206 bp fragment were purified by low-melting agarose gelelectrophoresis followed by phenol-extraction. The purified fragments were as a template for the amplification of a 1491 bp fragment employing oligonucleotide-primers F8–547S and F8-2020AS using reaction-conditions as described above. The resulting 1491 bp fragment was digested with ApaII (position 8353) and KpnI (position 1811) and the and the resulting ApaII-KpnI was used to replace the corresponding ApaII-KpnI fragment of pCLB-BPVdB695. The resulting plasmid was termed pCLB-BPVdB695RI562 and the sequence of the ApaII-KpnI fragment that contained the Arg$^{562}$->Ile mutation was verified by olignucleotide-sequencing.

C127 cells were maintained in Iscove's medium supplemented with 10% fetal calf serum, 100 U/ml penicillin and 100 μg/ml streptomycin. Subconfluent monolayers of C127 cells were transfected employing calcium-phosphate essentially as described (Graham and Van der Eb, 1973, Virology vol. 52, 456–467). Plasmid pCLB-BPVdB695RI562 (20 μg) was cotransfected with pGKhyg (1 μg; Ten Riele et al., 1990, Nature vol. 348, 649–651). Following transfection and selection of transfected cells with 200 μg/ml of hygromycin, individual clones were isolated and propagated in selective medium. The secretion of Factor VIII was monitored by measuring the ability of Factor VIII to function as a cofactor for the Factor IXa-dependent conversion of factor Xa, employing a chromogenic substrate for Factor Xa (Coatest Factor VIII, Chromogenix, Mölndal, Sweden). Factor VIII antigen was determined using monoclonal antibodies that have been previously characterized (Lenting et al., 1994, J. Biol. Chem. vol 269, 7150–7155). Monoclonal antibody CLB-CAg12, directed against the Factor VIII light-chain was used as a solid phase, while peroxidase-labeled monoclonal antibody CLB-CAg117, also directed against the Factor VIII light-chain was used to quantify the amount of Factor VIII bound. Normal plasma derived from a pool of 40 healthy donors was used as a standard. Clones derived of cells transfected with pCLB-BPVdB 695RI562 that produced significant amounts of Factor VIII were stored in liquid nitrogen until use. One clone derived of cells transfected with pCLB-BPVdB695RI562 was grown till confluency and subsequently cofactor activity and antigen was determined as outlined above. The Factor VIII-protein modified at amino-acid position Arg$^{562}$ displayed a cofactor-activity of 56 mU/ml. The antigen-level was subsequently determined to be 72 mU/ml.

Our data show that cofactor molecules modified at their cleavage sites for activated protein C can be expressed in eukaryotic cells. These variant cofactor molecules are most conveniently purified by immuno-affinity chromatography methods, as have been previously established (Mertens et al., 1993. Br. J. Haematol. vol. 85, 133–142). Following purification, the modified cofactor proteins can be formulated into a therapeutic preparation for counteracting haemostatic disorders.

EXAMPLE 7

Construction of a factor V molecule with a mutation at a cleavage site for activated protein C.

As shown in Example 1, cofactor molecule with a mutation at a cleavage site for activated protein C may occur in plasma of patients suffering from thrombo-embolic disease as well as in normal healthy blood donors. In Example 4, it is revealed that such a modified cofactor obtained from plasma displays increased thrombin-generation when compared to the modified molecule. Furthermore, in Example 5 it is shown that a Factor V molecule carrying the substitution Arg$^{506}$→Gln is able to function as a "Factor VIII bypassing agent". Access to such variants may be restricted according to their prevalence in the normal donor population. This limitation can be overcome by producing such variants by recombinant DNA technology. An example of this strategy is provided by the following description, which outlines the construction of a Factor V cDNA containing a substitution at the cleavage site $Arg^{506}$ for activated protein C. This description is exemplary to an average expert in the art for the creation of similar substitutions at other cleavage sites in the cofactor molecule Factor V. Factor V cDNA is isolated essentially as described (Jenny et al., 1987. Proc. Natl. Acad. Sci. USA, vol. 84, 4846–4850). The 5' end of the Factor V cDNA is modified by the use of a double-stranded synthetic linker (5' AATGTCGACAAAGCCACCATG 3', sense; SEQ ID NO: 8 5' GTGGCTTTGTCGACATT 3', anti-sense) SEQ ID NO: 9 which is inserted into the NspI site that overlaps with the initiation-codon of Factor V. The 3'end of the Factor V cDNA is modified as follows: oligonucleotide-primer FV-7 (5' AATGCGGCCGCGGGGTTTTTGAATGTTCA 3'nucleotide 6679–6697; anti-sense) SEQ ID NO: 10 is used in conjunction with oligonucleotide-primer FV-8 (5' GTG-GCTAGATATATTAGGATC 3' nucleotide 6109–6130; sense) SEQ ID NO: 11 to amplify a 588 bp fragment. Reaction conditions are: 2' 90° C., 20' 55° C., 3' 72° C.; 37 times 45" 90° C., 90" 55° C., 3' 72° C.; 5' 65° C. in the presence of 1 mM dNTPs, 10 times Pfu-polymerase reaction buffer, 50 pMol of primer FV-7 and FV-8 and 2.5 U of Pfu-polymerase (Stratagene, Cambridge, UK). The resulting fragment is digested with XhoI and NotI (nucleotide 6137–6697) of Factor V) and the resulting fragment is used in a ligation together with a SphI-XhoI fragment (nucleotide 5134–6137 of Factor V), a SalI-SphI fragment (nucleotide 1–5134) containing the modified 5' end of the Factor V cDNA and the vector pBPV which is digested with XhoI and NotI (Pharmacia-LKB, Upsala, Sweden). The resulting construct is termed pCLB-PBVFV.

In order to construct a Factor V cDNA which contained a mutation at the APC-cleavage-site at $Arg^{506}$ of Factor V, oligonucleotide-primer 506-11 (5' CTGTATTCCTTGCCT-GTCCAG 3' nucleotide 1591–1612; anti-sense) SEQ ID NO: 12 is used in conjunction with oligonucleotide-primer FV-2 (5' TTGCAAGCTGGGATGCAGGCT 3'; nucleotide 946–967; sense) SEQ ID NO: 13 to amplify a 666 bp fragment. Reaction conditions are: 2' 90° C., 20' 55° C., 3' 72° C.; 37 times 45" 90° C., 90" 55° C., 3' 72° C.; 5' 65° C. in the presence of 1 mM dNTPs, 10 times Pfu-polymerase reaction buffer, 50 pMol of primer 506-11 and FV-2 and 2.5 U of Pfu-polymerase (Stratagene, Cambridge, UK). Similarly, oligonucleotide-primer 506-12 (5' CTGGACAG-GCAAGGAATACAG 3'; nucleotide 1591–1612; sense) SEQ ID NO: 14 and oligonucleotide-primer 506-2 (5' CAT-CACGTTTCACCTCATCAGG 3'; nucleotide 1708–1730: anti-sense) SEQ ID NO: 2 are used to amplify a 139 bp fragment using the reaction-conditions described above. Both the 139 bp fragment and the 666 bp fragment are used to amplify a 784 bp fragment employing oligonucleotide-primers 505-2 and FV-2. The resulting fragment is digested with KpnI (nucleotide-position 1674) and PstI (nucleotide-position 1068) and the Factor V-fragment which contains the $Arg^{506}$→Gln mutation is used to replace the corresponding fragment of the plasmid pCLB-BPV-FV. The resulting plasmid is termed pCLB-BPVFVRQ506 and. the sequence of the PstI-KpnI fragment that contained the $Arg^{506}$→Gln mutation is verified by oligonucleotide-sequencing.

Our data show that Factor V molecules modified at their cleavage sites for activated protein C can be constructed and cloned into an eukaryotic expression vector. These variant cofactor molecules are most conveniently expressed in eukaryotic cells by methods described (Kane et al., 1990. Biochemistry, vol. 29, 6762–6768). Purification of the modified proteins is preferably performed by immuno-affinity chromatography methods, as have been previously established for Factor V (Katzmann et al., 1981, Proc. Natl. Acad, Sci. U.S.A. vol. 78, 162–166).

BRIEF DESCRIPTION OF THE DRAWINGS

FIG. 1 shows the activation and inactivation sites for respectively thrombin and APC in factor VIII. At the top of the bar the cleavage-sites for thrombin in factor VIII are depicted. It has been shown that mutations at amino-acid position $Arg^{372}$ and $Arg^{1689}$, which interfere with the pro-coagulant function of this protein result in hemophilia A. At the bottom of the bar the cleavagesites of APC at position $Arg^{336}$ and $Arg^{562}$ have been depicted. Mutations at this site are likely to prolong the pro-coagulant activity of factor VIII, resulting in thrombophilia.

FIG. 2 shows the activation and inactivation sites for respectively thrombin and APC in factor V. At the top of the bar the cleavage-sites for thrombin are depicted. As yet no mutations have been documented at these amino-acid positions of factor V. At the bottom of the bar the cleavage-sites for APC at amino-acid position $Arg^{306}$, $Arg^{506}$, $Arg^{679}$ and $Arg^{1765}$ have been depicted. Mutations at these sites are likely to prolong the pro-coagulant activity of factor V resulting in thrombophilia.

FIG. 3 represents an analysis of a patient that does not carry a mutation at amino acid position $Arg^{506}$ of factor V (individual A) and a patient carrying the mutation (individual B). Lane 1. 154 bp fragment, amplified with oligonucleotide-primer 506-1 and 506-2, derived of cDNA of individual A. Lane 2. Same fragment of individual A, following digestion with NruI. Lane 3. 154 bp fragment amplified with oligonucleotide-primers 506-1 and 506-2, derived of cDNA from individual B. Lane 4. Same fragment of individual B following digestion with NruI. Lane 5. 100 bp ladder.

FIG. 4 gives a sequence analysis of patients factor V cDNA. Factor V cDNA derived from individual B, heterozygous for the $Arg^{506}$ to Gln mutation is shown in the right panel. Heterozygosity is scored by the occurrence of both a "G" and an "A" at the second base pair of codon $Arg^{506}$ (CGA/CAA) of factor V (as indicated by the arrow). In the left panel sequence analysis of individual A, who does not carry the mutation is displayed. The arrow indicates the single "G" observed at the second base pair of codon $Arg^{506}$ (CGA/CGA).

FIG. 5 shows the generation of thrombin in plasma containing factor V with or without mutation at the cleavage site for activated protein C at amino-acid position 506. Plasma was obtained from three distinct donors, with the factor V genotype $Arg^{506}/Arg^{506}$, $Arg^{506}/Gln^{506}$ and $Gln^{506}/Gln^{506}$.

FIG. 6 shows the generation of thrombin in partially purified factor V, prepared as a Prothrombin Complex Concentrate from plasma of donors selected for the factor V genotype $Arg^{506}/Arg^{506}$, $Arg^{506}/Gln^{506}$ and $Gln^{506}/Gln^{506}$.

FIG. 7 shows the generation of thrombin in the plasma of a patient with severe haemophilia A and a high-titer inhibitor against factor VIII. Thrombin formation is fully normalized by the presence of exogenous factor V provided that this carries the $Arg^{506}$ to Gln mutation at the cleavage site for activated protein C.

TABLE I

Cleavage-sites for APC in factor VIII and factor V. The cleavage-sites in human factor VIII have been identified by amino-acid sequencing of the cleavage products of APC digested factor VIII. Cleavage-sites in human factor V are based upon homology with bovine factor V. Amino-acid sequencing of proteolytic fragments generated by digestion of bovine factor V by APC has been used to determine the exact cleavage-sites. Amino-acid 1 of factor V and VIII correspond to the first amino-acid following the signal peptide. Nucleotide 1 of factor V and VIII correspond to the first nucleotide of the start-codon.

human factor VIII (amino-acid sequence $Ser^{328}$-$Asp^{345}$; nucleotides 1039–1090):
Ser-Cys-Pro-Glu-Glu-Pro-Gln-Leu-Arg ↓ Met-Lys-Asn-Asn-Glu-Glu-    SEQ ID NO. 15
Ala-Glu
AGC TGT CCA GAG GAA CCC CAA CTA CGA    ATG AAA AAT AAT GAA GAA    SEQ ID NO. 16
GCG GAA
human factor VIII (amino-acid sequence $Cys^{554}$-$Arg^{571}$; nucleotides 1717–1768):
Cys-Tyr-Lys-Glu-Ser-Val-Asp-Gln-Arg ↓ Gly-Asn-Gln-Ile-Met-Ser-    SEQ ID NO. 17
Asp-Lys
TGC TAC AAA GAA TCT GTA GAT CAA AGA    GGA AAC CAG ATA ATG TCA    SEQ ID NO. 18
GAC AAG
human factor V (amino-acid sequence $Ile^{298}$-$Gln^{315}$; nucleotides 976–1027):
Ile-Lys-Asn-Cys-Pro-Lys-Lys-Thr-Arg ↓ Asn-Leu-Lys-Lys-Ile-Thr-    SEQ ID NO. 19
Arg-Glu
ATT AAA AAC TGC CCA AAG AAA ACC AGG    AAT CTT AAG AAA ATA ACT    SEQ ID NO. 20
CGT GAG
human factor V (amino-acid sequence $Cys^{498}$-$Glu^{515}$; nucleotides 1576–1627):
Cys-Lys-Ser-Arg-Ser-Leu-Asp-Arg-Arg ↓ Gly-Ile-Gln-Arg-Ala-Ala-    SEQ ID NO. 21
Asp-Ile
TGT AAG AGC AGA TCC CTG GAC AGG CGA    GGA ATA CAG AGG GCA GCA    SEQ ID NO. 22
GAC ATC
human Factor V (amino acid sequence $Pro^{671}$-$Glu^{688}$; nucleotides 2095–2146)
Pro-Glu-Ser-Thr-Val-Met-Ala-Thr-Arg ↓ Lys-Met-His-Asp-Arg-Leu-    SEQ ID NO. 23
Glu-Pro
CCA GAA TCT ACA GTC ATG GCT ACA CGG AAA ATG CAT GAT CGT TTA    SEQ ID NO. 24
GAA CCT
human factor V (amino-acid sequence $Glu^{1757}$-$Ser^{1774}$; nucleotides 5353–5404)
Glu-Lys-Lys-Ser-Arg-Ser-Ser-Trp-Arg ↓ Leu-Thr-Ser-Ser-Glu-Met-    SEQ ID NO. 25
Lys-Lys
GAA AAG AAG TCC CGA AGT TCT TGG AGA    CTC ACA TCC TCA GAA ATG    SEQ ID NO. 26
AAA AAA

TABLE II

List of oligonucleotide primers used to detect mutations at APC cleavage-sites at amino-acid position $Arg^{506}$ of factor V and $Arg^{336}$ and $Arg^{562}$ of factor VIII. Mismatches in the oligonucleotide-primers with respect to the wild-type sequence of factor V and VIII are underlined. Following PCR amplification of the designated primers with an appropriate oligonucleotideprimer derived from the wild-type factor V and VIII sequence, a fragment is generated that carries a restriction-site. The presence of a mutation at a particular codon, destroys this restriction-site and thus can be used to monitor mutations at cleavage-sites for APC.

human factor VIII (amino-acid sequence $Ser^{328}$-$Asp^{345}$; nucleotides 1039–1090):
Ser-Cys-Pro-Glu-Glu-Pro-Gln-Leu-Arg ↓ Met-Lys-Asn-Asn-Glu-Glu- SEQ ID NO. 15
Ala-Glu
AGC TGT CCA GAG GAA CCC CAA CTA CGA    ATG AAA AAT AAT GAA GAA    SEQ ID NO. 16
GCG GAA
oligonucleotide-primer 336-1 (sense; nucleotide 1039–1064):
AGC TGT CCA GAG GAA CCC CAA CT<u>T</u> C    SEQ ID NO. 27
restriction-site: TaqI      <u>T</u> CGA
oligonucleotide-primer 336-2 (sense; nucleotide 1039–1063):
AGC TGT CCA GAG GAA CCC CAA GTA    SEQ ID NO. 28
restriction-site: RsaI      <u>G</u>TA C
oligonucleotide-primer 336-3 (anti-sense; nucleotide

TABLE II-continued

| | |
|---|---|
| 1180–1201):<br>AGT TTT AGG ATG CTT CTT GGC | SEQ ID NO. 29 |
| human factor VIII (amino-acid sequence $Cys^{554}$-$Arg^{571}$;<br>nucleotides 1717–1768):<br>Cys-Tyr-Lys-Glu-Ser-Val-Asp-Gln-Arg ↓ Gly-Asn-Gln-Ile-Met-Ser-<br>Asp-Lys | SEQ ID NO. 17 |
| TGC TAC AAA GAA TCT GTA GAT CAA AGA   GGA AAC CAG ATA ATG TCA<br>GAC AAG | SEQ ID NO. 18 |
| oligonucleotide-primer 562-5 (sense; nucleotides 1717-14 1741)<br>TGC TAC AAA GAA TCT GTA GAT CGA<br>restriction-site: MboII     GA AGA | SEQ ID NO. 30 |
| oligonucleotide-primer 562-6 (anti-sense; nucleotides<br>2020–2038)<br>GTG TTT GAA GGT ATA TCC | SEQ ID NO. 31 |
| human factor V (amino-acid sequence $Cys^{498}$-$Glu^{515}$; nucleotides<br>1576–1627):<br>Cys-Lys-Ser-Arg-Ser-Leu-Asp-Arg-Arg ↓ Gly-Ile-Gln-Arg-Ala-Ala-<br>Asp-Ile | SEQ ID NO. 21 |
| TGT AAG AGC AGA TCC CTG GAC AGG CGA   GGA ATA CAG AGG GCA GCA<br>GAC ATC | SEQ ID NO. 22 |
| oligonucleotide-primer 506-1 (sense; nucleotides 1576–1600):<br>TGT AAG AGC AGA TCC CTG GAC TCG<br>restriction-site NruI     TCG CGA | SEQ ID NO. 1 |
| oligonucleotide-primer 506-2 (anti-sense; nucleotides 1708–<br>1730)<br>C ATC ACG TTT CAC CTC ATC AGG | SEQ ID NO. 2 |

TABLE III

Oligonucleotide primers derived from both factor V cDNA and genomic sequences to diagnose the $Arg^{506}$ to Gln substitution. The part of the primer derived from nucleotide 1–8 of intron 10 of the factor V gene is indicated in bold. Oligonucleotide-primer 506-8 contains a "C" to "T" substitution with respect to oligonucleotide-primer 506-7, that corresponds to the $Arg^{506}$ to Gln substitution described in the text (underlined).

| | |
|---|---|
| primer 506-5 5' ATCAGAGCAGTTCAACCAGGG 3'<br>(sense; nucleotide 1414–1435 factor V<br>cDNA) | SEQ ID<br>NO. 3 |
| primer 506-6 5'AAAAGTACCTGTATTCCT 3'<br>(anti-sense; nucleotide 1602–1612 of<br>factor V cDNA and nucleotide 1–8 of<br>intron 10 of the factor V gene) | SEQ ID<br>NO. 32 |
| primer 506-7 5' AAAAGTACCTGTATTCCTC 3'<br>(anti-sense; nucleotide 1601–1612 of<br>factor V cDNA and nucleotide 1–8 of<br>intron 10 of the factor V gene) | SEQ ID<br>NO. 33 |
| primer 506-8 5' AAAAGTACCTGTATTCCT<u>T</u> 3'<br>(anti-sense; nucleotide 1602–1612 of<br>factor V cDNA and nucleotide 1–8 of<br>intron 10 of the factor V gene) | SEQ ID<br>NO. 34 |

What is claimed is:

1. A pharmaceutical composition comprising a blood coagulation Factor V which carries a substitution mutation of an arginine residue in at least one position selected from the group consisting of residues 306, 506 and 1765: wherein the pharmaceutical composition is resistant against activated protein C.

2. A pharmaceutical composition according to claim 1, wherein the mutation is at position 306.

3. A pharmaceutical composition according to claim 1, wherein the mutation is at position 506.

4. A pharmaceutical composition according to claim 1, wherein the mutation is at position 306 and at position 506.

5. A pharmaceutical composition according to claim 1, wherein said factor V is obtained from genetically engineered cells or organisms expressing factor V that is resistant against activated protein C.

6. A pharmaceutical composition according to claim 1, wherein said factor V is obtained from blood or plasma of individuals displaying resistance against activated protein C.

7. A pharmaceutical composition according to claim 1, which further comprises at least one additional coagulation factor.

8. A pharmaceutical composition according to claim 7, wherein said at least one additional coagulation factor is selected from the group consisting of factor II, factor VII, factor IX and factor X.

9. A pharmaceutical composition according to claim 1, which further comprises a pharmaceutically acceptable carrier, diluent or adjuvant.

10. A pharmaceutical composition according to claim 1, for the treatment of disorders in the blood coagulation cascade.

11. A pharmaceutical composition according to claim 10, wherein said disorder in the blood coagulation cascade is due to a deficiency of at least one coagulation factor selected from the group consisting of factor VIII, factor IX, factor VII and factor X.

12. A pharmaceutical composition according to claim 11, wherein said disorder is complicated by the presence of inhibitors or antibodies against said coagulation factor.

13. A pharmaceutical composition for the treatment or prophylaxis of disorders in the blood coagulation cascade in a mammal requiring prophylaxis or treatment comprising a blood coagulation Factor in accordance with claim 1.

* * * * *

UNITED STATES PATENT AND TRADEMARK OFFICE
CERTIFICATE OF CORRECTION

PATENT NO. : 6,083,905
DATED : July 4, 2000
INVENTOR(S) : Voorberg, et. al.

It is certified that error appears in the above-identified patent and that said Letters Patent is hereby corrected as shown below:

In Column 6, Line 44,   Now reads "Factor VIII bypassing acgents",
                        should read --Factor VIII bypassing agents--.

In Column 8, Line 13,   Now reads "general the close",
                        should read --general the dose--.

In Column 9, Line 56,   Now reads " "GI to "A" substitution",
                        should read --"G" to "A" substitution--.

In Column 12, Line 8,   Now reads ""Cryosupernatarnt plasmas",
                        should read --Cryosupernatant plasmas --.

Signed and Sealed this

Twenty-second Day of May, 2001

*Attest:*

NICHOLAS P. GODICI

*Attesting Officer*   Acting Director of the United States Patent and Trademark Office